United States Patent [19]

Sadee

[11] Patent Number: 5,882,944
[45] Date of Patent: Mar. 16, 1999

[54] METHODS FOR G PROTEIN COUPLED RECEPTOR ACTIVITY SCREENING

[75] Inventor: Wolfgang Sadee, Ross, Calif.

[73] Assignee: The Regents of the University of California, Oakland, Calif.

[21] Appl. No.: 447,277

[22] Filed: May 22, 1995

Related U.S. Application Data

[63] Continuation-in-part of Ser. No. 261,500, Jun. 16, 1994, abandoned, which is a continuation-in-part of Ser. No. 81,612, Jun. 23, 1993, abandoned.

[51] Int. Cl.$^6$ .................. G01N 33/566; G01N 33/53
[52] U.S. Cl. .................. 436/501; 435/7.1; 514/2
[58] Field of Search .................. 514/66, 2; 436/501; 435/7.1

[56] References Cited

U.S. PATENT DOCUMENTS 5,061,715  10/1991  Sunkara et al. .................. 514/314

OTHER PUBLICATIONS

Biedler et al., "Morphology and Growth, Tumorigenicity, and Cytogenetics of Human Neuroblastoma Cells in Continuous Culture," *Cancer Res.*, 33, pp. 2643–2652 (1973).
Costa et al., "Drug Efficacy at Guanine Nucleotide–Binding Regulatory Protein–Linked Receptors: Thermodynamics Interpretation of Negative Antagonism . . . ," *Molec. Pharmacol.*, 41, pp. 549–560 (1992).
Frey et al., "A μ–Opioid Receptor in 7315c Tumor Tissue Mediates Inhibition of Immunoreactive Prolactin Release and Adenylate Cyclase Activity," *Endocrin.*, 115, pp. 1797–1804 (1984).
Kogan et al., "Elevated Basal Firing Rates and Enhanced Responses to 8–Bromo–cAMP in *Locus coeruleus* Neurons in Brain Slices from Opiate Dependent Rats," *Eur. J. Pharmacol.*, 211, pp. 47–53 (1992).
Nestler, "Molecular Mechanisms of Drug Addiction," *J. Neurosci.* 12:7, pp. 2439–2450 (1992).
Rasmussen et al., "Opiate Withdrawal and the *Locus coeruleus*: Behavioral, Elactrophysiological, and Biochemical Correlates," *J. Neurosci.*, 10, pp. 2308–2317 (1990).
Sibinga et al., "Opioid Peptides and Opioid Receptors in Cells of the Immune System," *Ann. Rev. Immunol.*, 6, pp. 219–249 (1988).
Yu et al., "A Human Neuroblastoma Cell Line Expresses μ and δ Opioid Receptor Sites," *J. Biol. Chem.*, 261, pp. 1065–1070 (1986).
Yu et al., "Efficacy and Tolerance of Narcotic Analgesics at the μ Opioid Receptor in Differentiated Human Neuroblastoma Cells," *J. Pharmacol. Exp. Ther.*, 245, pp. 350–355 (1988).
Yu et al., "Differentiation of Human Neuroblastoma Cells: Marked Potentiation of Prostaglandin E–Stimulated Accumulation of cAMP by Retinoic Acid," *J. Neurochem.*, 51, pp. 1892–1899 (1988).
Yu et al., "Regulation of Cyclic AMP by the μ–Opioid Receptor in Human Neuroblastoma SH–SY5Y Cells," *J. Neurochem.*, 55:4, pp. 1390–1396 (1990).

Schütz et al., "Reverse Intrinsic Activity of Antagonists of G Protein–Coupled Receptors," *TiPS*, 13 (Oct. 1993), pp. 376–379.
Chen et al., "Moleculare Cloning and Functional Expression of a μ–Opioid Receptor from Rat Brain," *Molecular Pharmacology*, 44, pp. 8–12 (1993).
Wang et al., "Constitutive μ Opioid Receptor Activation as a Regulatory Mechanism Underlying Narcotic Tolerance and Dependence," *Life Sciences*, 54:20, pp. 339–350 (1994).
Smith et al., "Problems and Approaches in Studying Membrane Opioid Receptors," *Molecular Approaches to Drug Abuse Research vol. I*, edited by Lee et al., U.S. Dept. of Health & Human Services, pp. 69–84 (1991).
Hawkins et al., "[$^3$H]–[H–D–Phe–Cys–Try–D–Trp–Orn–Thr–Pen–Thr–NH$_2$] ([$^3$H]CTOP), A Potent and Highly Selective Peptide for Mu Opioid Receptors in Rat Brain," *J. Pharmacol. & Exp. Ther.*, 248:1, pp. 73–80 (1989).
Abdelhamid et al., "Characteristics of μ and δ Opioid Binding Sites in Striatal Slices of Morphine–Tolerant and –Dependent Mice," *Eur. J. Pharmacol.*, 198, pp. 157–163 (1991).
Sharma et al., "Dual Regulation of Adenylate Cyclase Accounts for Narcotic Dependence and Tolerance," *Proc. Antl. Acad. Sci. USA*, 72:8, pp. 3092–3096 (1975).
Sadée et al., "Constitutive Activation of the μ–Opioid Receptor: A Novel Paradigm of Receptor Regulation in Narcotic Analgesia, Tolerance, and Dependence," *Analgesia*, 1:1, pp. 11–14 (1994).
Lameh et al., Abstract of "Agonist Induced Conversion of the Hm1 Muscarinic Cholinergic Receptor to a Constitutively Active State: A Novel Papadigm of Receptor Regulation," p. 47 of the program for *Subtypes of Muscarinic Receptors: The Sixth International Symposium*, Sponsered by Boston University School of Medicine and Johann Wolfgang–Goethe University, held in Fort Lauderdale, Florida, Nov. 9–12, 1994.
Baker, Mitzi, "New Hypothesis on How Narcotics Produce Tolerance, Dependency," *Synapse* (newspaper of the Universiy of California, San Francisco), 39:15 (Jan. 12, 1995), pp. 1 and 5.

(List continued on next page.)

*Primary Examiner*—Cecilia J. Tsang
*Assistant Examiner*—Michael Borin
*Attorney, Agent, or Firm*—Majestic, Parsons, Siebert & Hsue

[57] ABSTRACT

A method for screening G protein coupled receptors is provided in which G protein coupled receptors that are constitutively active are determined, such as by measuring receptor phosphorylation agonist independent signalling. When a G protein coupled receptor is found to be regulated by constitutive activity, then assay systems may be set up to classify test compounds as agonists, neutral antagonists, or negative antagonists with respect to G protein coupled receptor signalling and phosphorylation. Such determinations and screening are useful for selecting new pharmaceuticals potentially useful in treating disease states mediated by G protein coupled receptors, with applications including treatments in conjunction with narcotic analgesia.

12 Claims, No Drawings

OTHER PUBLICATIONS

Högger et al., "Activating and Inactivating Mutations in N– and C– terminal i3 Loop Junctions of Muscarinic Acetylcholine Hm1 Receptors," *J. Biol. Chem.*, 270:13, (1995), pp. 7405–7410.

Wang et al., "Agonist Induced Constitutive Activation of the μ Opioid Receptor by Phosphorylation," *Regulatory Peptides,* 54:1, (1994), pp. 323–324.

Wang et al. Constitutive m opioid receptor activation . . . Life Sciences, 54: 339–350, Apr. 10, 1994.

Costa et al. Antagonists with negative intrinsic activity at delta opiod receptors coupled to GTP–binding proteins. Proc. Niatl. Acad. Sci., USA, 86: 7321–7325, Oct. 1989.

Sharma S.K. Dual regulation of adenylate cyclase accounts for narcotic dependence and tolerance. Proc. Natl. Acad. Sci. USA, 72 (8): 3092–3096, Aug. 1975.

METHODS FOR G PROTEIN COUPLED RECEPTOR ACTIVITY SCREENING

This is a continuation-in-part of Ser. No. 08/261,500, filed Jun. 16, 1994, now abandoned, which is a continuation-in-part of Ser. No. 08/081,612, filed Jun. 23, 1993, abandoned of common assignment herewith.

This invention was made with Government support under Grant Nos. DA 04166 and GM43102, awarded by the U.S. Department of Health and Human Services. The Government has certain rights in this invention.

FIELD OF THE INVENTION

The present invention generally relates to G protein coupled receptors, and more particularly to assays for determining certain activities of G protein receptors, which determinations may be applied to modulating the activities of G protein coupled receptors for therapeutic benefit.

BACKGROUND OF THE INVENTION

G protein coupled receptors (hereinafter sometimes termed "GPCR"s) comprise a large superfamily of receptors sharing a common structural motif of seven transmembrane helical domains. When a ligand (an agonist) binds to a GPCR and activates it, signal transduction is achieved through the intermediary G protein (a heterotrimeric GTP binding protein) which in turn activates the second messenger system. Although the exact nature of the receptor-G protein interactions is not yet known, the receptor activated regulatory cycle of the G protein involves GTP exchange for GDP, dissociation of the $\alpha$ and $\beta\gamma$ subunits, activation of the second messenger pathway by GTP-$G_\alpha$ and $\beta\gamma$, and termination of activation upon GTP hydrolysis to GDP by the inherent GPTase activity of the $\alpha$ subunit. G protein coupled receptors regulate virtually all bodily functions ranging from vision and olfaction to neuronal and endocrine signaling.

A general property of signal transduction mediated by G protein coupled receptors is the attenuation of signaling upon prolonged agonist stimulation. These processes are referred to as desensitization, tachyphylaxis, adaptation, tolerance, or quenching. Because signal attenuation limits the clinical uses of many pharmaceuticals acting on GPCRs, the mechanism for this process has been the focus of much research. Receptor phosphorylation by selective kinases of G protein coupled receptors (termed "GRK"s) has been shown to contribute to desensitization of several receptors. To date, no selective and or potent GRK inhibitors have been reported, other than heparin which does not penetrate into intact cells, even though such inhibitors might prevent desensitization in these cases (e.g., the $\beta 2$ receptor). GRKs selectively polyphosphorylate only the active receptor state, which not only serves as a preferred substrate, but also directly stimulates GRK activity.

Another emerging recognized feature of a number of GPCRs is the presence of a basal level of signalling activity, occurring in the absence of any agonist ligand. Mutations inducing high basal activity have been associated with genetic disorders, demonstrating the physiological relevance of basal receptor activity. For GPCRs displaying basal activity, two classes of antagonist have been defined, i.e., neutral antagonists which block only agonist induced effects without changing basal activity, and inverse agonists, or negative antagonists, which also block basal receptor activity.

Prior assay attempts to detect any significant changes of the $\mu$ opioid receptor system during prolonged agonist exposure have been unable to determine biochemical mechanisms underlying narcotic addiction. Thus, much of the current research work has focused on events downstream of the receptor, such as long-term gene regulation, in attempting to account for the dependent state. Because the dependence liability of narcotic drugs severely limits their clinical utility as potent analgesics and exerts a heavy toll on society through illicit narcotic drug use, a screen for agents that could prevent or reverse the narcotic dependent state or might facilitate gradual withdrawal would greatly enhance the clinical utility of narcotic analgesics and could serve as an effective pharmacological weapon in the fight against illicit drug use.

SUMMARY OF THE INVENTION

The present invention is directed to certain G protein coupled receptors where exposure to agonist leads to persistent constitutive activation of the receptors by phosphorylation.

G protein coupled receptors that are within the scope of this invention include all subtypes of the opioid, muscarinic, dopamine, adrenergic, cAMP, opsins, angiotensin, serotonin, thyrotropin, gonadotropin, substance-K, substance-P and substance-R receptors, melanocortin, metabotropic glutamate, or any other GPCR receptors known to couple via G proteins.

"Constitutive activation" as used herein means an agonist induced, polyphosphorylated receptor state where agonist is no longer required for continuous signal transduction. Because many disorders may be mediated by the imbalance of the ratio of agonist activatable receptors to constitutively activated receptors (designed herein as "GPCR/GPCR*"), this ratio may be clinically manipulated in accordance with the invention for therapeutic applications.

One aspect of the present invention is to provide a screening assay for determining whether particular G protein coupled receptors are constitutively activatable by prior agonist exposure. This regulatory process is fundamentally different from the already known basal activity of many GPCRs.

Another aspect of the present invention is to provide a screening assay for classifying compounds as agonists, neutral antagonist, or negative antagonist, each having differential effects on signalling and phosphorylation of the G protein coupled receptor. Because this expanded categorization explicitly considers the effect of the constitutively activated, polyphosphorylated GPCRs, rather than the basal activity which results from spontaneous flipping on of unmodified receptors, it is more informative than the prior art classification of agonist and neutral and negative antagonist. Moreover, differential effects of ligand on several downstream events had not been considered previously.

Another aspect of the present invention is to provide a method for modulating the ratio of GPCR/GPCR*.

In a preferred embodiment of the present invention, use of screening assays permits the identification of several agonists, neutral antagonists, negative antagonists, and G protein kinase inhibitors capable of reducing the constitutively active $\mu^*$ state of the $\mu$ opioid receptor, as the driving force in the development of narcotic tolerance and dependence. An agent shown to prevent and reverse the conversion of $\mu$ opioid receptors to the constitutively active $\mu^*$ opioid receptors in vitro, has been shown to prevent and/or reverse narcotic tolerance and dependence in animal models.

Accordingly, practice of the invention is useful to determine or to screen for new pharmaceuticals useful for treating disease states mediated by G protein coupled receptors capable of constitutive activation, to enhance the clinical utility of existing pharmaceuticals targeted to G protein coupled receptors, such as via modulations of the GPCR/GPCR* ratio, and to devise therapeutic treatments from agents selected by means such as the screening methods of the invention.

DETAILED DESCRIPTION OF THE PREFERRED EMBODIMENTS

The principal novel tenet of the subject invention is that receptor phosphorylation can cause constitutive activation of some GPCRs, rather than desensitization. The phosphorylated receptor is thereby locked into the active state, R*, as if occupied by an agonist, which is distinct from basal activity. A powerful positive feed-forward loop evolves, by which R* is continuously signalling and simultaneously stimulates its own polyphosphorylation. As a result, the polyphosphorylated R* can be kept in the active state for prolonged time periods, even though single phosphorylation and dephosphorylation steps are fast. Moreover, exposure to agonists enhances formation of R* by further stimulating receptor phosphorylation. This kinetic trapping mechanism represents a novel, potent, long-lasting positive regulatory mechanism with potentially profound and wide-ranging physiological implications. Any receptor undergoing this type of constitutive activation would be expected to contribute dominantly to the overall basal tone in the body, thereby modifying tonicity caused by continuously released hormones and neurotransmitters.

The invention generally relates to the discovery of agonist induced conversion of G protein coupled receptors to a constitutively active, polyphosphorylated state, R*. In certain G protein receptors, an agonist induces signal transduction and simultaneously induces self-phosphorylation by G protein receptor kinases which are selective for the activated form of the receptor. While phosphorylation generally leads to receptor desensitization, phosphorylation of this class of G protein coupled receptors leads to constitutive activation. Independent of receptor agonist, constitutively activated GPCRs can transduce signal for a prolonged period of time.

The basis for any assay for constitutive activation of G protein coupled receptors is receptor phosphorylation and/or the activity of the constitutively active G protein coupled receptors. A non-obvious key element of such an assay is to pretreat the receptor preparation with an agonist, followed by complete removal of the agonist, and subsequently to measure constitutive activity with the use of neutral and negative antagonists.

One simple assay is to measure the constitutive activity of the G protein coupled receptor after pretreatment with (a) agonist alone, (b) agonist and G protein receptor kinase inhibitor to inhibit R* formation, either in the absence or presence of a neutral or negative antagonist. Because constitutive activation is mediated by phosphorylation, phosphatase inhibitors should enhance constitutive activation and G protein receptor kinase inhibitors should suppress constitutive activation, if the G protein coupled receptor indeed has constitutive activity. A variation of this assay is to measure the direct phosphorylation of the G protein coupled receptor instead of the activity of the G protein coupled receptors. If negative and neutral antagonist are unknown, screens of known receptor antagonists are required to identify prototypal agents with neutral and negative activity against R*.

Once a G protein coupled receptor is found to be regulated by constitutive activity, assay systems may be set up to screen for compounds with the desired selective properties. For instance, an agonist may be found that activates the GPCR without also inducing receptor phosphorylation. Such an agonist would prevent the formation of GPCR*.

Morphine is an example of an agonist which induces signal transduction in addition to inducing receptor phosphorylation, which can account for its tolerance and dependence liability. Moreover, classical antagonists with respect to the GPCR in its ground state (ligands that bind to GPCR with no activity) can be additionally categorized for their simultaneous effects on the constitutively activated GPCRS* (notwithstanding previous classifications of neutral and negative antagonists with regard to basal receptor activity which did not consider receptor polyphosphorylation).

If it has no effect on GPCRs*, then the antagonist is classified as a neutral antagonist. If it blocks the activity of GPCRS*, then the antagonist is classified as a negative antagonist (or inverse agonist). Moreover, these antagonists can also be tested for their ability to suppress continued GPCR* phosphorylation.

Among the G protein coupled receptors that are capable of constitutive activation are the opioid receptors. For example, continuous stimulation of the $\mu$ opioid receptor with morphine results in enhanced conversion to the constitutively active state $\mu^*$, as a principal new mechanism underlying the tolerant-dependent state. Thus, the $\mu$ opioid receptor system serves as an example for identifying novel agents that affect formation of the constitutively active receptor state and any resultant long-term effects, such as tolerance and dependence to narcotic agonists.

Naloxone is an example of a negative antagonist which blocks constitutive signalling of $\mu^*$, but does not suppress or even enhances continuous $\mu^*$ phosphorylation, as determined by the assays described here. Therefore, naloxone causes immediate and severe withdrawal in the dependent state, but it fails to reverse the dependent state which continues beyond the duration of naloxone in the body. Therefore, the proposed assays would predict such in vivo properties of antagonist and permit the selection of antagonists that could actively reverse the dependent state by suppressing continuous $\mu^*$ phosphorylation.

Thus, the GPCR/GPCR* ratio can be manipulated by any combination of full agonist, neutral agonist, neutral antagonist, negative antagonist, GRK kinase inhibitor, or phosphatase inhibitor. If an imbalance of GPCR/GPCR* causes a certain disease state, the present invention provides the methods for modulating the GPCR/GPCR* ratio to treating that disease state.

Although the invention will be specifically described using $\mu$ opioid receptors, it may be generalized to any G protein coupled receptor that is capable of constitutive activation upon stimulation with an agonist. G protein coupled receptors that are within the scope of this invention include all subtypes of the opioid, muscarinic, dopamine, adrenergic, cAMP, opsins, angiotensin, serotonin, thyrotropin, gonadotropin, substance-K, substance-P and substance-R, melanocortin, metabotropic glutamate, vasoactive intestinal peptide, secretin, and any other GPCR receptors.

In describing practice of this invention, a source of opioid $\mu$ receptors in combination with a means of monitoring constitutively active $\mu^*$ receptors, such as G protein activity (GTPase activity or GTP exchange) or the cAMP second messenger system, will together sometimes hereinafter be termed the "biological system." One source of opioid $\mu$ receptors that are exposed to or coupled with cAMP production is a human neuroblastoma (NB) cell line (SK-N-SH) and its NB subclone SH-SY5Y, both which express abundant opioid $\mu$ receptors (about 50,000 sites per cell). When intact cells are grown under appropriate cell culture conditions, the cells will be producing cAMP. Another source of a useful biological system for purposes of this invention can be certain tissues from experimental animals (e.g. rats and mice, which are good models for opioid $\mu$ receptor activity in humans), such as rat locus coeruleus or guinea pig ileum.

When whole cells are used as the biological system, then it is desirable to add an adjuvant or stimulating agent of adenylyl cyclase, such as PGE, VIP, or forskolin, which stimulate cAMP production and therefore facilitate assay of the inhibitory effect of the $\mu$ receptor. The phosphodiesterase inhibitor IBMX is frequently added to further enhance cAMP levels; however, as shown below, IBMX was determined by the assays in this application to be a $\mu$ receptor kinase inhibitor (and hence a prototype of a new class of potential anti-addictive agents); therefore, it must be avoided in the assay. Neuroblastoma cells are preferably first differentiated with, for example, 1–10 $\mu$M retinoic acid to enhance stimulatory and inhibitory receptor coupling to the cAMP system. Such preparations of a biological system have been described by Yu et al., *J. Neurochem.*, 51, pp. 1892–1899 (1988); Yu et al., *J. Neurochem.*, 55, pp. 1390–1396 (1990); and Yu and Sadée, *J. Pharmac. Exp. Ther.*, 245, pp. 350–355 (1988).

A particularly preferred source of opioid $\mu$ receptors that are exposed to or coupled with cAMP production is the HEK293 cell line stably transfected with the $\mu$ receptor gene. However, any cell line that expresses naturally occurring $\mu$ opioid receptors or cloned $\mu$ opioid receptors will work. When intact cells are grown under appropriate cell culture conditions, the cells will be producing cAMP. Another source of $\mu$ opioid receptors are certain tissues from animals such as rat locus coeruleus or guinea pig ileum.

In the opioid system, binding of a agonist (such as morphine) to the $\mu$ opioid receptor leads to the inhibition of adenylyl cyclase which ultimately results in decreased levels of cAMP. Upon prolonged agonist exposure, the cAMP system is unregulated to compensate for the agonist induced inhibition. Ultimately, the effects of the increase numbers of $\mu^*$ receptors and the unregulated cAMP cancel each other out, at least partially. Consequently, a relatively small spontaneous overshoot of cAMP is observed in an agonist exposed receptor system upon the removal of the agonist (hereinafter referred to as the "spontaneous overshoot"). This spontaneous overshoot of cAMP is the difference between the cAMP levels of a dependent receptor system upon the removal of an agonist and the control levels of cAMP in the absence of any agonist, and is one of the accepted biological markers for narcotic dependence. In order to detect constitutive $\mu^*$ activity continuously suppressing cAMP production even after agonist removal, one adds a negative antagonist, such as naloxone (its negative character being defined by the present assays). By suppressing $\mu^*$ inhibitory signalling, naloxone causes an additional cAMP overshoot, referred to here as the naloxone cAMP overshoot, indicative of $\mu^*$ and the dependent state.

Using cAMP as a surrogate measure for receptor activity, one assay embodiment in accordance with the invention involves the measurement of three values. A first cAMP value is determined by measuring the effects of a first portion of receptors on cAMP production in the absence of agonist pretreatment. This first cAMP value acts as a control value. Second and third cAMP values are also determined after agonist pretreatment and agonist removal. The second cAMP value is determined by measuring the effects of a second portion of receptors on cAMP production while the receptors are in a constitutively active state but are substantially free of agonist molecules. The difference between the second cAMP value and the first cAMP value represents the upregulated activity of the cAMP second messenger system, resulting from agonist pretreatment, which is however partially suppressed by $\mu^*$ activity. Presence of such constitutive $\mu^*$ activity represents a novel aspect which had not been suspected previously. The third cAMP value is determined by measuring the effects of a third portion of the receptors on cAMP production while they are in a constitutively active state, are substantially free of any agonist molecules, and are in the presence of a sufficient quantity of a negative antagonist to associate negative antagonist molecules with substantially all the receptors. The difference between the third cAMP value and the second cAMP value represents the activity of the constitutively active $\mu^*$ opioid receptors.

BY "substantially free" of agonist molecules is meant that there is less than about 0.1% to about 0.3% of the total agonist drug remaining after pretreatment with a near maximally effective dose so that there would be no measurable effect in response curves. One can make removal determinations through use of radioactively labeled agonist tracer, or radioimmune assays, or one can analyze the wash water for residual agonist by using it to expose naive cells and determining whether there is an agonist effect. Typically, by washing cells carefully three times, substantial agonist removal is accomplished. If one is performing the assay in vivo, then the tissue is removed, sliced, and is washed in a water bath.

Because the conversion of $\mu$ to $\mu^*$ activity is mediated by phosphorylation, kinase inhibitors should prevent receptor phosphorylation while phosphatase inhibitors should enhance this process. As predicted, these results have been observed in vitro systems. For example, the general kinase inhibitor H7 completely prevents the formation of $\mu^*$ receptors and rapidly reverses $\mu^*$ activity in SH-SY5Y cells. As a result, co-administration of kinase inhibitors with existing analgesics should permit the use of these analgesics without the development of tolerance and dependence. Alternatively, kinase inhibitors should serve as effective agents for treating narcotic addiction.

Suitable G protein receptor kinases for practicing the invention in addition to the general kinase inhibitor H7, include the xanthine analog, 3-isobutyl-1-methyl-xanthine (IBMX). Although generally recognized and used as cAMP phosphodiesterase inhibitor (Beavo et al., *Molec. Pharmacol.*, 6, 597 (1971)), IBMX is recognized here for the first time as a $\mu$ receptor kinase inhibitor which suppresses $\mu^*$ formation. Thus, IBMX represents a prototypal agent of a class of drug congeners with broad pharmacological implications, including caffeine, theophylin, theobromine, etc. This invention now permits the selection of alkylated xanthines and congeners with preferential activity against receptor kinases, rather than cAMP phosphodiesterases. Such inhibitors may function as general GPCR kinase inhibitors, and therefore, may also be applicable to other GPCRs that are activatable by GPCR kinases, e.g., as proposed for the dopamine receptor. For example, in a manner analogous to the coadministration of a kinase inhibitor with a narcotic analgesic to prevent or to retard the development of tolerance, the coadministration of a GPCR kinase inhibitor with L-dopa is believed useful in treating Parkinsonism. Moreover, in disease states characterized by hyper-activity of dopamine neurotransmission, administration of a GPCR kinase inhibitor is thought to reduce the dopamine receptor hyperactivity, and thereby, alleviate disease symptoms. Alternatively, such kinase inhibitors could also serve to suppress desensitization during drug agonist treatment, for example of the β2 adrenergic receptor, which is thought to desensitize upon phosphorylation.

Finally, direct measurements of $\mu$ receptor phosphorylation can be used. Using the cloned $\mu$ receptor gene transfected into HEK293 cells, phosphorylation of the $\mu$ receptors can be directly measured. As predicted by the proposed mechanism, the $\mu$ receptor is continuously phosphorylated by $\mu$ receptor kinases (GRKS) because it already preexists in part in the polyphosphorylated $\mu^*$ state and rapidly exchanges phosphate. Moreover, the addition of kinase inhibitor H7, and of IBMX, inhibited $\mu^*$ receptor phosphorylation. Consequently, the direct measurement of $\mu$ receptor phosphorylation can also serve as another screen for compounds that can manipulate the $\mu/\mu^*$ ratio.

Suitable phosphatase inhibitors for practicing the present invention include calyculin-A. Since the PPase-2 selective okadaic acid at a low concentration (15 nM) is ineffective in enhancing $\mu^*$, it appears that PPase-1 is responsible for dephosphorylating $\mu^*$ in SH-SY5Y cells. However, phosphatases may vary in different tissues, and with different receptors.

Accordingly, an inventive assay system can be readily set up to classify compounds for their effects on G protein coupled receptors, such as on the $\mu$ opioid receptors. Using any one or a combination of the three markers, cAMP (second messenger system), receptor phosphorylation and G protein receptor kinase activity, compounds may be classified (as agonist, neutral antagonist, negative antagonist) for their effects both on the agonist activatable $\mu$ receptors and the constitutively active $\mu^*$ receptors. For a more general assay of GPCR signalling, instead of cAMP assays, one can substitute assays of G protein activity, such as GTPase activity or GTP exchange, which represent the more proximal receptor signalling events and are generally applicable to all GPCRs, regardless of their second messenger system.

Using such an assay, compounds may be screened for their selective effects on either the $\mu$ or $\mu^*$ receptors. For instance, agonist for the $\mu$ opioid receptors may be found that do not also have the ability to induce or limit $\mu$ opioid receptor phosphorylation. Such an agonist would not induce narcotic tolerance or dependence and would thus be an excellent analgesic for treating patients with chronic pain. Similarly, the assay can also be used to screen for compounds that can be used in conjunction with known full agonists (such as morphine) to prevent the development of tolerance and dependence by inhibiting the formation of the constitutively active $\mu^*$ receptors. These compounds may include GPCR kinase inhibitors to prevent receptor phosphorylation.

If the goal is to search for compounds to treat a narcotic dependent individual, then the same assays may be used to screen for neutral antagonists that will bind to the agonist activatable $\mu$ opioid receptor to prevent agonist action while at the same time not eliciting the symptoms of withdrawal by blocking the, activity of the constitutively active $\mu^*$ opioid receptors. Thus, compounds can be determined that have the properties of blocking the effects of a narcotic analgesic such as morphine or of both morphine and naloxone with no effect when given alone, so as to be considered useful for treating overdoses of narcotic analgesics while avoiding the risk of excessive precipitated withdrawal. This class of compounds should be useful to prevent or reverse the generation of constitutively active receptors and thus can be used therapeutically in conjunction with a narcotic analgesic to suppress the addictive liability of the narcotic analgesic.

Thus, a therapeutic method for treating a patient addicted to a narcotic drug is provided since one can use assays of the invention to select an agent determined to prevent and/or to reverse constitutive activity of opioid receptors and then administer a therapeutically effective amount of the selected agent to the addicted patient. Further, one may treat patients addicted to a narcotic drug, who are suffering from an overdose (or suspected overdose) of the narcotic drug by selecting a neutral $\mu$ receptor antagonist that does not block $\mu^*$ activity. Preferably, the agent selected would also reverse the $\mu^*$ state to the normal $\mu$ receptor state. In another aspect, a therapeutic method for providing analgesia to a patient can comprise selecting a $\mu$ receptor agonist that results in lower conversion of the $\mu$ receptor to its constitutively active state than does a narcotic analgesic such as morphine, and administering such $\mu$ receptor agonist for the treatment for pain, with the desirable properties of reduced tolerance and dependence. Yet further, a therapeutic method for providing analgesia to a patient is by selecting a kinase inhibitor and administering a narcotic analgesic in conjunction with the selected kinase inhibitor. The kinase inhibitor selected is effective to retard development of tolerance to the narcotic analgesic administered, such as for preventing the formation of constitutively active opioid receptors.

Because the process of constitutive activation lends itself to screening anti-addictive agents and probing the molecular mechanisms of narcotic dependence, practice of the invention is expected to provide a new approach to separating the beneficial activity of narcotics from undesirable long-term effects.

Pharmaceutically effective amounts of agents selected (as by the screening method herein discussed) may be readily determinable clinically by establishing safe dosages and dose-response curves, such as in established clinical pain models. For example, analgesia in rodent animal models can be measured by the tail-flick method of D'Amour and Smith, *J. Pharmac. Exp. Ther.*, 72, pp. 74–79 (1941), and as modified by Tulunay and Takemori, *J. Pharmac. Exp. Ther.*, 190, pp. 395–400 (1974), both incorporated herein by reference. $ED_{50}$ values, their 95% confidence limits, and significance of potency relation between two $ED_{50}$ values may be determined by the method of Litchfield and Wilcoxon, *J. Pharmac. Exp. Ther.*, 96, pp. 99–113 (1949), incorporated herein by reference.

By "narcotic analgesic" as used herein and exemplified by morphine, is meant in addition to morphine, the morphine salts (such as morphine hydrobromide, morphine hydrochloride, morphine mucate, morphine oleate, morphine N-oxide, and morphine sulfate), and morphine analogs such as normorphine, diacetyldihydromorphine, diacetylmorphine hydrochloride, codeine, and diacetylmorphine (heroin). Other widely used narcotic analgesics with which the present invention may be used include alphatrodine, methadone, merperidine, leverthanol, propoxyphene, fentanyl, oxymorphone, anileridine, and metopon.

Administration of the selected agent in conjunction with administering a dose of a narcotic analgesic can be within at least about 30 minutes of the narcotic analgesic dose. Preferably, the administering is by administering a single, admixed dose where the narcotic analgesic is morphine, a morphone analog, or a morphine salt. Thus, administrations may be intravenous and formulations of pharmaceutically acceptable solutions, carriers, or salts as are well known to the art may be used. Depending upon the agent selected, other forms of administration may be found to be clinically useful.

Moreover, antagonists may be found that block continuous $\mu^*$ phosphorylation. G protein receptor kinase inhibitors may also be included in the treatment regimen to prevent any further conversion of $\mu$ to $\mu^*$ receptors.

In summary, any combination of agonist, neutral antagonist, negative antagonist, GPCR kinase inhibitors, and phosphatase inhibitors may be used to manipulate the $\mu/\mu^*$ ratio. Because the development of narcotic tolerance and dependence is characterized by the slow conversion of the $\mu$ to $\mu^*$ receptors, most of the compounds for therapeutic benefit are focused on the prevention of the formation of the $\mu^*$ receptors. However, this focus is only with respect to the $\mu$ opioid receptors. In other G protein coupled receptors, it may be desirable to form GPCR* in order to maintain the GPCR/GPCR* at the optimal level. Depending on whether the disease state is mediated by the abundance of one receptor state versus the other, different combinations of agonist, neutral antagonist, negative antagonists, GRK kinase inhibitors, and phosphatase inhibitors will be used. Since the present invention discloses the general mechanism for these G protein coupled receptors, persons skilled in the art will be able to ascertain which combinations of agonist, neutral antagonist, negative antagonist, GRK inhibitors, and phosphatase inhibitors to use to achieve the desired ratio of GPCR/GPCR*.

It is to be understood that the description and the following examples are intended to illustrate and not limit the scope of the invention.

EXAMPLE 1

Regulation of cAMP in Cell Culture

Although the basic assay will be described using SK-N-SH or SH-SY5Y cells, it is readily adaptable to other cell lines or tissue samples as the useful biological systems. The cells were grown at 37° C. in DME H-21 medium supplemented with 10% fetal calf serum containing 100 $\mu$g/ml streptomycin and 100 IU/ml penicillin. Optimal sensitivity to $\mu$ opioid agonist inhibition of cAMP accumulation was observed in retinoic acid pretreated cells (5 $\mu$M for 6 days), and upon adenylyl cyclase stimulation with prostaglandin $E_1$ ($PGE_1$), in the absence of any phosphodiesterase inhibitor.

To induce a tolerant-dependent state, the cells were pretreated with 1 $\mu$M morphine for period ranging from 2 minutes to 48 hours. The relatively low pretreatment concentration of 1 $\mu$M morphine was selected to achieve near maximal effects in tolerant cells while facilitating complete washout of the drug. Immediately before the cAMP accumulation assay, cells were washed twice with medium containing 5% serum and twice more with serum free medium. Supernatants from the washed cells failed to elicit any opioid agonist like cAMP response when transferred to fresh untreated cells, suggesting effective morphine removal during washing. Use of $^3$H-morphine also indicated that 0.1% of the pretreatment concentration was left in the final assay medium, which was below effective morphine levels in this cell line. The values for cAMP levels were determined by radioimmunoassay after stimulation with 1 $\mu$M prostaglandin $E_1$ over 15 minutes in the presence or absence of naloxone.

After pretreatment of SH-SY5Y cells for 6 to 12 hours with morphine, and complete drug removal by thorough washing of the cells, a spontaneous cAMP overshoot was observed when compared to untreated cells. Moreover, addition of naloxone to the pretreated and thoroughly washed, drug-free cells caused a significant additional increase of cAMP accumulation in proportion to the level of tolerance/dependence developed by the cells (this naloxone induced cAMP overshoot ranged from 20 to 80% in over 40 experiments, p<0.001). The difference between the naloxone induced cAMP overshoot and the spontaneous cAMP overshoot represents the activity of the $\mu^*$ receptors in suppressing cAMP levels that is now blocked by the negative antagonist naloxone. Therefore, the naloxone cAMP overshoot provides a novel measure of constitutive receptors' activity observed after agonist pretreatment.

The naloxone cAMP overshoot was also observed in extensively washed membrane homogenates obtained from morphine pretreated cells, further arguing against residual morphine as a cause. Moreover, results with neutral antagonists CTAP and CTOP which do not affect cAMP levels (described below) rule out residual opioids residing at the receptor as the cause for the naloxone cAMP overshoot. When naloxone was applied to thoroughly washed, untreated SH-SY5Y control cells, a decrease of cAMP accumulation was observed. The decreased cAMP levels relative to control levels by an antagonist indicates presence of some constitutive activity in untreated cells which is in equilibrium with the agonist activatable $\mu$ receptors. Such small basal receptor activity paradoxically enhances cAMP production in this case. Paradoxical stimulation of cAMP production by GPCRs normally thought to be inhibitory have been observed repeatedly with varying receptors and cell culture conditions. In the case of the $\mu$ receptor, such changes from stimulatory to inhibitory actions (in response to agonists) have been proposed to contribute to narcotic tolerance and dependence.

To account for tolerance and dependence, the spontaneous and the naloxone cAMP overshoot should occur gradually. Pretreatment of cells with 1 $\mu$M morphine for 20 minutes or less caused a small decrease of $PGE_1$ stimulated cAMP accumulation, which was not reversed or even enhanced by the addition of naloxone. Therefore, this decrease could not have resulted from residual morphine. Morphine pretreatment longer than 20 minutes caused gradually increasing levels of both the spontaneous and the naloxone cAMP overshoot, until a maximum is reached at 12 hours. A treatment period of 12 hours for maximal cAMP overshoot is compatible with the slow development of tolerance and dependence.

The spontaneous cAMP overshoot disappeared within 30 minutes after morphine removal. This result supports the hypothesis that the spontaneous cAMP overshoot is not responsible for the prolonged dependent state. In contrast, the naloxone cAMP overshoot lasted for at least two hours. From 4–12 hours after morphine removal, naloxone had no effect on cAMP levels, in contrast to the decrease in cAMP levels observed in untreated cells. This observation is consistent with the delayed peak of narcotic withdrawal seen in vivo, which occurs after morphine is largely eliminated from the body.

Because many G protein coupled receptors are also linked to the signal pathway via cAMP, the differential ligand effects on cAMP levels can be readily adapted for any particular G protein coupled receptor. As described above, any cells that are capable of producing cAMP under cell growth conditions (the useful biological system) and that abundantly express either naturally occurring G protein coupled receptors or cloned G protein coupled receptors may be used. Another major second messenger pathway involves turnover of phosphatidyl inositol (PI), e.g., for the muscarinic m1 receptor. The activity of all GPCRs can be assessed by measuring GTPase activity and GTP exchange.

One variation of the assay involves the identification of a negative antagonist as described above. The most efficient method for finding negative antagonists would be to screen known antagonists of the particular G protein coupled receptors for negative intrinsic activity. Antagonists may be identified using standard competition assays that are well known in the art. If the binding of an agonist to the G protein coupled receptors results in increasing the levels of cAMP relative to control levels of cAMP, then compounds that decrease the levels of cAMP relative to control levels of cAMP in the absence of agonist would indicate negative intrinsic activity. If the binding of an agonist to the G protein coupled receptors results in decreasing the levels of cAMP relative to control levels of cAMP, then compounds that increase the levels of cAMP relative to control levels of cAMP in the absence of agonist would indicate negative intrinsic activity.

With respect to $\mu$ opioid receptors, the basic assay described in Example 1 can be readily adapted to classify compounds as agonist, negative antagonist, and neutral antagonist depending on their effects on the levels of cAMP.

A full agonist is an agonist that activates signal transduction and induces receptor phosphorylation leading to a slow conversion of $\mu$ to $\mu^*$ receptors upon prolonged exposure. Using the cAMP levels, a full agonist would inhibit cAMP levels and would induce a naloxone induced cAMP overshoot in the dependent state.

In contrast, a novel type of agonist activates only signal transduction but would not induce receptor phosphorylation. Because there would be no slow conversion from $\mu$ to $\mu^*$ receptors, the naloxone cAMP overshoot would not be observed if naloxone is added to an agonist exposed system in the absence of agonist. Although ideally, such an agonist would be optimal, any agonist that slows the formation of $\mu^*$ receptors relative to such existing analgesics like morphine would also be a therapeutically useful.

Antagonists for the $\mu$ opioid receptors may also be additionally classified as either neutral antagonist or negative antagonist depending on their effect on the constitutively activated $\mu^*$ opioid receptors. A neutral antagonist is a classical antagonist with respect to the agonist activatable $\mu$ opioid receptors and does not block the signalling activity of the constitutively active $\mu^*$ opioid receptors. In contrast, a negative antagonist is a classical antagonist with respect to the agonist activatable $\mu$ opioid receptors and blocks the signalling activity of the constitutively active $\mu^*$ opioid receptors. Moreover, neutral and negative antagonists can be classified as to their effect on $\mu^*$ phosphorylation. For example, while naloxone is a negative antagonist with respect to signalling, it failed to suppress $\mu^*$ phosphorylation. Therefore, it produces withdrawal, but does not reverse the dependent state.

The $\mu$ selective agonist peptide DAMGO was also tested for its ability to induce signalling and receptor phosphorylation in $\mu$ and EE$\mu$ receptor transfected HEK293 cells. DAMGO was slightly more potent and efficacious than morphine in both activity tests, when added acutely to the assay incubations. However, in a separate experiment, it was shown that DAMGO, but not morphine induced massive receptor recycling through endocytic vesicles. Since recycling of the $\beta 2$ receptor was associated with dephosphorylation, it is possible that during long-term exposure to an agonist such as DAMGO, overall $\mu^*$ formation is lower than with morphine. While this remains to be tested, the distinct downstream effects of morphine and DAMGO demonstrate that different agonists do affect different downstream pathway even at the same receptor.

The ability of the neutral antagonist CTAP to affect $\mu^*$ phosphorylation during the assay incubation was also tested. While CTAP did not block $\mu^*$ phosphorylation, it consistently lowered the level of $\mu^*$ phosphorylation relative to naloxone. This result suggests that CTAP may affect the balance of $\mu$ and $\mu^*$ receptors in favor of the ground state $\mu$, and therefore, it is potentially useful not only in the treatment of narcotic overdose in addicts, but also as an agent capable of at least partially reversing the tolerant-dependent state.

Classification as either neutral antagonist or negative antagonist can be determined by the addition of the compound to a agonist-free but narcotic dependent cell system (as in Example 1) that has been pretreated with morphine for at least 12 hours. If there is no additional cAMP overshoot above the spontaneous cAMP overshoot, then the compound is a neutral antagonist. If there is an additional cAMP overshoot above the spontaneous cAMP overshoot, then the compound is a negative antagonist.

EXAMPLE 2

Screening for Compounds Using cAMP Levels as a Marker

Using the assay of Example 1, a panel of opioid drugs were classified for their ability to either decrease or increase cAMP levels in morphine pretreated SH-SY5Y cells. As expected from their high potency in causing withdrawal, naloxone, naltrexone, and diprenorphine demonstrated negative intrinsic activity by increasing cAMP levels in drug-free dependent cells. Consequently, naloxone, naltrexone, and diprenorphine were classified as negative antagonists. Buprenorphine, DAMGO and DADLE were classified as full agonists and are either as effective if not more so than morphine. Nalorphine, CTAP and its analogs, CTOP and d-Tic-CTAP were classified as neutral antagonists because they had no significant effect on cAMP levels in dependent cells.

Similarly, the cAMP levels could be used to classify compounds with respect to any particular G protein coupled receptor that transduces signal via the cAMP pathway. If the binding of an agonist to the G protein coupled receptors results in increasing the levels of cAMP relative to control levels of cAMP, then an antagonist that decrease the levels of cAMP relative to control levels of cAMP in the absence of agonist would be a negative antagonist. If the binding of an agonist to the G protein coupled receptors results in decreasing the levels of cAMP relative to control levels of cAMP, then an antagonist that increase the levels of cAMP relative to control levels of cAMP in the absence of agonist would be a negative antagonist. If the antagonist had no effect on the levels of cAMP relative to control levels, then the antagonist would be a neutral antagonist.

Alternatively, measurement of PI turnover could replace cAMP assays where appropriate (m1 receptor). Lastly, direct assays of G protein activity (GTPase and GTP exchange) are universally applicable to all GPCRs. Negative antagonists would suppress, and agonists would enhance G protein activity, while neutral antagonists would be without effect.

A full agonist with respect to a particular G protein coupled receptor is an agonist that also induces receptor phosphorylation and the resulting slow conversion of GPCR to GPCR*. This may be established by monitoring the levels of cAMP after prolonged exposures to the agonist. The cAMP levels are measured relative to the levels after removal of agonist after prolonged exposure. If there an additive change in the levels of cAMP when a negative antagonist is added, then the agonist is a full agonist. If there is no additional change or even a subtractive change in the levels of cAMP when a negative antagonist is added, then the agonist is a neutral agonist. A subtractive effect might result if there are significant preexisting basal levels of GPCR*. PI coupled receptors can be analyzed in an endogenous fashion, or arrays of G protein activities are used.

EXAMPLE 3

Effects of H7 and CTAP in Morphine Tolerant Dependent Mice

Withdrawal

Male ICR mice in groups of 10 each were made acutely dependent on morphine by subcutaneous injection of 100 mg/kg morphine sulfate. After 4 hours, naloxone was given either intraperitoneally or simultaneously by intracerebroventricular and intrathecal injections to induce withdrawal. Alternatively, CTAP was injected. To test the ability of kinase inhibitors to reverse the dependent state, animals were injected 3.5 hours after the first 100 mg/kg morphine dose with saline or with H7 or H8. At 4 hours, withdrawal was precipitated by injection of naloxone (3 mg/kg intraperitoneally). Mice were then placed in Plexiglass cylinders and observed for a 15 minute period with the number of vertical jumps recorded.

Tolerance

Mice in groups of 10 were again injected subcutaneously with 100 mg/kg morphine sulfate, and analgesia was measured with the tail immersion assay at 55° C. by determining the time elapsed before the tail is flicked (15 seconds cutoff=100% analgesia). At 4.5 hours after the first dose, either saline alone or saline containing 50 nM H7 was injected. At 5 hours after the analgesic effect of first morphine dose had essentially ceased and a second dose of 10 mg/kg morphine sulfate was injected to determine the degree of tolerance.

Results

The formation of $\mu^*$ can account for narcotic dependence, and paradoxically also for tolerance. Assuming that all $\mu$ receptors were converted to $\mu^*$, it follows that further addition of an agonist would be without effect, because all receptor are already active, and the organism is adapted to this activity. If $\mu^*$ activity were responsible for narcotic tolerance and dependence, then the following effects in morphine pretreated animals would be predicted. First H7 should reverse tolerance and suppress naloxone induced jumping without affecting morphine analgesia whereas H8 should be without any effect. Second, the neutral antagonist CTAP should cause less withdrawal than naloxone because it does not reverse the activity of $\mu^*$. Finally, CTAP should reverse naloxone induced jumping.

Administration of H7 30 minutes before naloxone strongly suppressed the number of naloxone precipitated jumps without affecting gross behavior of the animals or morphine antinociception as measured in the 55° C. hot water tail-flick test. In contrast, H8 was without effect on naloxone induced jumping. Therefore, the protein kinase inhibitor H7 reversed the drug dependent state towards the naive state within 30 minutes. H7 also fully reversed morphine tolerance observed 5 hours after a 100 mg/kg morphine sulfate dose in mice. The test dose of 10 mg/kg morphine sulfate produced only 22±14% analgesia in the tail flick assay when given 5 hours after the first dose, and 30 minutes after a control injection of saline. However, injection of 50 nM H7 30 minutes before the second morphine test dose completely reversed tolerance yielding 90±10% analgesia. Therefore, H7 reversed both morphine tolerance and dependence in an acute mouse model as predicted.

As expected for a neutral antagonist, CTAP caused significantly less withdrawal jumping, from 77±20 jumps for naloxone to 32±12 jumps, and it partially reversed naloxone induced withdrawal jumping. These combined results document that the predictions from the in vitro results can be verified in an animal model of narcotic tolerance and dependence. This is the first time that agents have been successfully used to reverse tolerance and dependence, selected on the basis of a novel mechanism of $\mu$ receptor phosphorylation and constitutive activation.

EXAMPLE 4

Radiolabeled agonists tracers can alternatively be used to rapidly screen for agents with an ability to bind to the constitutively active GPCR*. Agonists are expected to have low affinity to the constitutively active receptors and can serve as an analytical tool to block the GPCR to allow the selective labeling of the constitutively active GPCR*. The constitutively active GPCR* are selectively labeled with radiolabeled neutral or negative antagonists, using agonist pretreated preparations to maximize $\mu^*$. Thus, when the receptors are exposed to a test composition, one is able to determine whether the test composition binds to the selectively labeled receptors. Those compounds that bind to the selectively labeled GPCR* could then be further classified as a neutral antagonist or negative antagonist depending on their effects on the activity of GPCR*. Because this assay is much faster than the cAMP type assays, it can be used as the first screen when testing a large number of compounds.

EXAMPLE 5

Direct Measurement of $\mu$ Receptor Phosphorylation

Epitope-tagged $\mu$ opioid receptor (EE-$\mu$R)

The sequence, TTTTAAGCTT ACCATG GAAT ACATGCCAATGGAAGACAGC AGCACCGGCC CAGGG (SEQ ID NO: 1), containing a HindIII restriction site, the start codon, and a sequence encoding the epitope EYMPME (underlined portion), served as the 5' primer in order to append the epitope tag to the amino terminal of the rat $\mu$ receptor by the polymerase chain reaction. The 3' primer sequence, GCTCTAGAGC GAGGGTCTGG ATGGTG (SEQ ID NO: 2), contained a stop codon and an XbaI restriction site. The amplified fragment (EE-$\mu$R) was ligated into pRc/CMV which contains a neomycin-resistance gene, and subcloned into the E. coli TOP 10F' strain. The 5' sequence containing the epitope was verified by automated sequencing. Human embryonic kidney cells (HEK293) were transfected by the calcium phosphate method, and clonal cell lines stably expressing EE-$\mu$R were selected with 400 $\mu$g/ml G-418 and maintained in DMEM/H-16/F-12 with 10% fetal calf serum and 200 $\mu$g/ml G-418.

Lipand Binding Assays and cAMP assay

EE-$\mu$R expression was quantified with [3H]-diprenorphine. HEK293 cells stably expressing EE-$\mu$R were harvested in PBS, and triplicate samples were incubated with 10 nM [$^3$H]-diprenorphine and differing concentrations of diprenorphine or morphine sulfate in 50 mM Tris, pH 7.4. Cells were incubated for 2 hours at 20° C. and harvested on GF/C glass filters which were washed three times with cold PBS, and the tritium content determined. Displacement data were fit to the logistic function, $B=B_{max}-[B_{min}* L]/[IC_{50}+L]+NSB$, where B is the tracer bound, L=diprenorphine or morphine concentration, and NSB is the nonspecific binding. Protein content was determined by the Bradford method. Bradford, *Anal. Biochem.*, 72, pp. 248–254 (1976).

Immunoprecipitation of the Phosphorylated EE-μR

Phosphorylation of EE-μR was performed in permeabilized cells by a modification of the procedure described by Raymond. Raymond, *J. Biol. Chem.*, 266, pp. 14747–14753 (1991). Confluent flasks with approximately $2\times10^7$ HEK293 cells were washed gently in 50 mM Tris (pH 7.4), 100 mM NaCl and incubated for 15 minutes at 37° C. in phosphate-free DMEM. After harvesting and brief centrifugation cell pellets were resuspended in phosphate-free medium and aliquots of digitonic were added until approximately 90% of cells were permeabilized as defined by failure to exclude trypan blue dye. Final digitone concentration was 150–200 μM. Cells were treated with 10 μM morphine sulfate or buffer and 1 μCi/μl[γ-$^{32}$P]-ATP in a final volume of 500 μl for 15 minutes at 25° C. with gentle rocking. Labeling medium was removed and cell pellets were washed twice in ice cold Tris-NaCl buffer containing phosphatase and protease inhibitors (50 mM Tris, pH 7.4, 100 mM NaCl, 10 mM sodium pyrophosphate, 10 mM NaF, 1 mM benzamidine, 1 μg/ml leupeptin, and 1 μg/ml aprotinin). Cells were resuspended in ice-cold lysis buffer containing phosphatase inhibitors, incubated on ice for 10 minutes, and homogenized in a Dounce homogenizer. A membrane pellet was prepared, solubilized in 10 mM CHAPS, and immunoprecipitated with 1:40 dilution of anti-EE monoclonal antibody. The incorporation of $^{32}$P into the supernatant was determined at the time of immunoprecipitation of equalized control and transfected samples. The 8% SDS-PAGE gels were autoradiographed and bands were quantified by scanning densitometry.

Results

The epitope-tagged EEm receptor was similar to the wild-type μ receptor in all pharmacological assays. Confirming predicted results, the epitope tagged μ opioid receptor is significantly phosphorylated in the absence of any agonist, suggesting the presence of μ*. Agonist exposures (15 minutes) during the labeling assay increased the levels of phosphorylation of the receptors by nearly twofold. Moreover, pretreatment with 1 μM morphine for 6–12 hours, followed by agonist removal before the phosphorylation assay, enhanced μ receptor phosphorylation by threefold, indicative of agonist dependent conversion of μ to μ*. Naloxone did not block μ receptor phosphorylation, but in contrast appeared to slightly stimulate it. This result is consistent with the finding that naloxone does not reverse the dependent state in vivo. As predicted GRK kinase inhibitor H7 strongly inhibits μ receptor phosphorylation, either when added acutely to the assay, or via pretreatment and subsequent removal before the assay. This result suggest that μ receptor kinase inhibition depletes the μ* state.

As a result, assays may be modified to use direct receptor phosphorylation as a marker for classifying compounds as full agonist, neutral agonist, negative antagonist, neutral antagonist, and GOCR kinase inhibitor. Although these results are with respect to the μ opioid receptors, they may be readily modified for any particular G protein coupled receptor. Moreover, G protein receptor kinase inhibitors may be found directly using standard enzyme activity assays. See generally, Chen et al., J. Biol. Chem., 268: 7825–7831 (1993).

There are at least 7 genes encoding the family of related G protein receptor kinases that all have the same characteristics essential for supporting the positive feed-forward mechanism of sustained GPCR* activity. These are expressed differentially in different tissues, providing the opportunity for selective effects; however, no selective inhibitors are available. This invention permits the selection of such kinase inhibitors and their evaluation as potential therapeutic agents.

Mental disorders involving the dopaminergic system include schizophrenia and Parkinsonism, which are associated with an excess and deficit, respectively of dopaminergic transmission. Moreover, dopaminergic pathways are thought to be essentially involved in reward mechanisms and drug cravings. However, the mechanisms underlying these processes are not understood.

As with the μ opioid receptors which involve narcotic tolerance and dependence, an imbalance of the agonist activatable dopamine receptor (DR) and constitutively active dopamine receptors (DR*) may be involved in schizophrenia, Parkinsonism, and drug cravings. Excess constitutively active dopamine receptor activity could be involved in schizophrenia, and drug seeking behavior/addiction. As an example, constitutive activation of the dopamine receptors could also explain why treatment of Parkinsonism with L-DOPA (which gets converted to dopamine) loses its effectiveness. Thus, in a manner analogous to the coadministration of a kinase inhibitor with a narcotic analgesic to prevent or to retard the development of tolerance, the coadministration of a GPCR kinase with L-dopa is believed useful in treating Parkinsonism, to prevent or retard the constitutively active state of dopamine receptors. Therefore, analogous to the results with the μ opioid receptors, manipulating the DR/DR* ratio could lead to treatment of schizophrenia and drug addiction, and to enhance existing therapies for Parkinson's disease.

Among the known dopamine receptor subtypes, the D2 receptor plays a prominent role in schizophrenia. Changes in D2 ligand binding characteristics that were observed in post-mortem CNS tissue from schizophrenic patients, have suggested that altered receptor-G protein coupling may play a role. Preliminary experiments analogous to those initially performed for the μ opioid receptors in stably transfected HEK293 cells, indicate that D2 receptors are also regulated through constitutive activation. While quinpirole served as the agonist (equivalent to morphine), haloperidol, spiperone, and sulpiride all displayed negative antagonism. Spontaneous and negative antagonist induced cAMP overshoots were observed after quinpirole pretreatment and thorough drug removal by washing. This result supports the view that the D2 receptor is also converted to a constitutively active state during agonist exposure. To determine D2 receptor phosphorylation, the same EE epitope tag was introduced into the D21 gene (long splice isoform), immediately adjacent to the ATG initiation codon. Thus, a similar set of assays can now be performed with the D21 receptor.

EXAMPLE 6

Using HEK293 cells stably transfected with the long splice isoform of the D2 receptor, incubation with a known antagonist, spiperone in the absence of agonist, resulted in decreased cAMP levels relative to control indicating intrinsic negative activity, as proposed for the μ receptor. The effects of the agonist quinpirole and antagonist spiperone on cAMP levels before and after pretreatment with quinpirole were nearly identical to that of morphine and naloxone in the μ opioid receptor system. Because the D2 receptor also transduces signal via the cAMP pathway, assays described for the μ opioid receptor system may thus be readily adapted for the D2 receptor.

As cholinergic pathways intimately associated with cognitive functions, cholinergic deficits are a hallmark of neurodegenerative disorders involved with memory impairment. Elevation in levels of acetylcholine are thought to enhance cognitive functions by postsynaptic action on the muscarinic m1 receptor. The muscarinic m1 receptor is coupled to phospholipase C which in turn stimulates phosphatidyl inositol (PI) turnover. One example of the attempt to modulate levels of acetylcholine for therapeutic benefit is tacrine, an acetylcholinesterase inhibitor, for the treatment of Alzheimer's disease.

EXAMPLE 7

An extensive study of the m1 receptor which includes nearly 100 mutations of the m1 receptor gene has been undertaken in an effort to understand m1 signal transduction and regulation. One mutant, m1-E360A, was found to be a partially activated receptor and was stably transfected into HEK293 cells for further studies. Because of its partial activity, m1-E360A in HEK293 cells has a basal activity for stimulating PI turnover significantly above background.

The availability of this mutant form of the m1 receptor facilitated finding negative antagonists. Because of their decreasing effects on m1-E360A basal activity, atropine and scopolamine were found to be negative antagonists. As expected if constitutive activity were due to phosphorylation, pretreatment with agonist carbochol and with the phosphatase inhibitor calyculin A enhanced the basal activity. Therefore, HEK293 cells transfected with the m1 wild-type or the activating mutant E360A can serve in the assays equivalent to those described for the $\mu$ receptor.

EXAMPLE 8

Depending on the particular condition to be treated, it will be desirable to either increase or decrease the formation of the constitutively active GPCR*. In either case, any combination of agonist, neutral antagonist, negative antagonist, GRK kinase inhibitor, and phosphatase inhibitor may be used to obtained the desired effect. The classification of the compounds as agonist, neutral antagonist, negative antagonist, each with respect to signalling and phosphorylation, GPCR kinase inhibitor, or phosphatase inhibitor, can be achieved by the methods discussed in prior examples. For example, practice of the present invention may yield agonists that would transduce the desired signal but without the resulting constitutive activation of the receptors. If known full agonists are to be used that stimulate both signalling and phosphorylation, they may be used in combination with GPCR kinase inhibitor to prevent the formation of the constitutively active receptors. If attenuation of constitutive activity is sought to be treated, neutral antagonist and/or GPCR kinase inhibitor may be used. However, if the goal is to form constitutively active GPCR*, then full agonist and/or phosphatase inhibitors may be used. Because the present invention discloses the general mechanism for these G protein coupled receptors, persons skilled in the art would know which combination of agonist, neutral antagonist, negative antagonist, GPCR kinase inhibitor, or phosphatase inhibitor should be used to achieve the desired result. Useful agents can be selected with the described assays.

EXAMPLE 9

3-Isobutyl-1-methylxanthine (IBMX) is commonly used during cAMP assays (at a concentration of 500 $\mu$M) to inhibit cAMP breakdown by the enzyme cAMP-phosphodiesterase. Thereby, one increases the levels of cAMP accumulating during the assay. A direct measurement of $\mu$ receptor phosphorylation, using the epitope tagged $\mu$ receptor gene and the $^{32}$P labeling assay, was conducted by techniques analogous to those already described. IBMX at 500 $\mu$M, supposed $\mu$ receptor phosphorylation. IBMX at that concentration appeared to be more effective than H7 at 100 $\mu$M because it prevented the naloxone cAMP overshoot, even when added only to the acute cAMP accumulation assay, and not as a pretreatment agent.

Thus, IBMX is active in preventing receptor phosphorylation and appears to be an inhibitor of the $\mu$ receptor kinase(s). This is of general importance, as this activity may also apply to receptors other than the $\mu$ opioid receptor (e.g., the dopamine or muscarinic receptors). Moreover, IBMX is an alkylated xanthine, and thus, a prototype of a family of important drugs and chemicals, including theophylline, caffeine, theobromine. Among these one may find congeners with enhanced selectivity for the GPCR kinases over phosphodiesterases. Such an agent could be effective in the treatment of drug addiction, and other diseases that may be associated with elevated basal levels of receptor activity because of receptor phosphorylation.

It is to be understood that while the invention has been described above in conjunction with preferred specific embodiments, the description and examples are intended to illustrate and not limit the scope of the invention, which is defined by the scope of the appended claims.

It is claimed:

1. A method for assaying the effects of test compounds on constitutively active m1 receptors, comprising:

providing a biological system comprising cells having a plurality of m1 receptors;

constitutively activating the receptors by incubating the cells with a m1 receptor agonist;

removing substantially all of the agonist from the cells;

determining an activity of the receptors while in a constitutively activated state in the absence of agonist;

exposing the cells to a test compound;

determining at least one effect of the test compound on the activity of the constitutively active receptors while said receptors remain substantially free of agonist; and, classifying the test compound as an agonist, neutral antagonist, or a negative antagonist.

2. The method as in claim 1 wherein the determining at least one effect of the test compound includes measuring an activity of a G protein coupled receptor kinase.

3. The method as in claim 1 wherein the determining an activity of the receptors while in a constitutively activated state includes measuring phosphorylation of the receptors.

4. The method as in claim 1 wherein the determining an activity of the receptors while in a constitutively activated state includes measuring phosphatidyl inositol levels.

5. The method as in claim 1 wherein the determining an activity of the receptors while in a constitutively activated state includes measuring GTPase activity.

6. The method as in claim 1 wherein the determining an activity of the receptors while in a constitutively activated state includes measuring GTP exchange.

7. A method for assaying the effects of test compounds on constitutively active D2 dopamine receptors, comprising:

providing a biological system comprising intact cells having a plurality of D2 dopamine receptors;

constitutively activating the receptors by incubating the cells with a D2 dopamine receptor agonist;

removing substantially all of the agonist from the cells;

determining an activity of the receptors while in a constitutively activated state in the absence of agonist;

exposing the cells to a test compound;

determining at least one effect of the test compound on the activity of the constitutively active receptors while said receptors remain substantially free of agonist; and, classifying the test compound as an agonist, neutral antagonist, or a negative antagonist.

8. The method as in claim 7 wherein determining at least one effect of the test compound includes measuring an activity of a G protein coupled receptor kinase.

9. The method as in claim 7 wherein the determining an activity of the receptors While in a constitutively activated state includes measuring phosphatidyl inositol levels.

10. The method as in claim 7 wherein the determining an activity of the receptors while in a constitutively activated state includes GTPase activity.

11. The method as in claim 7 wherein the determining an activity of the receptors while in a constitutively activated state includes GTP exchange.

12. The method as in claim 7 wherein the determining an activity of the receptors while in a constitutively activated state includes measuring phosphorylation of the receptors.

* * * * *

UNITED STATES PATENT AND TRADEMARK OFFICE
CERTIFICATE OF CORRECTION

PATENT NO. : 5,882,944 Page 1 of 1
DATED : March 16, 1999
INVENTOR(S) : Wolfgang Sadée et al.

It is certified that error appears in the above-identified patent and that said Letters Patent is hereby corrected as shown below:

<u>Column 18,</u>
Lines 33, 36 and 38, "m1" should read -- mu --

Signed and Sealed this

Third Day of February, 2004

JON W. DUDAS
*Acting Director of the United States Patent and Trademark Office*